United States Patent [19]

Agut

[11] Patent Number: 5,383,105
[45] Date of Patent: Jan. 17, 1995

[54] LAMP FOR SURGICAL ILLUMINATION WITH AUTOMATIC ADJUSTMENT OF THE CONCENTRATION OF LIGHT RAYS ON OPERATING FIELD

[75] Inventor: Gerard Agut, Uglas, France

[73] Assignee: STE Distributon Materiel Chirurgical (S.D.M.C.)(S.A.), Toulouse, France

[21] Appl. No.: 980,918

[22] Filed: Nov. 24, 1992

[30] Foreign Application Priority Data

Nov. 25, 1991 [FR] France ............... 91 14622

[51] Int. Cl.⁶ .......................... A61C 13/00
[52] U.S. Cl. ........................ 362/285; 362/33; 362/286; 362/804
[58] Field of Search ............ 362/33, 276, 285, 286, 362/311, 346, 386, 802, 804; 315/151, 324, 363

[56] References Cited

U.S. PATENT DOCUMENTS

| | | |
|---|---|---|
| 2,088,024 | 7/1937 | Baber ............ 362/285 |
| 4,159,511 | 6/1979 | Dejonc ............ 362/804 |
| 4,316,237 | 2/1982 | Yamada et al. ........... 362/33 |
| 4,395,750 | 9/1983 | Scheidemann et al. ....... 362/285 |
| 4,400,765 | 8/1983 | Kochem ............ 362/804 |
| 4,517,632 | 5/1985 | Roos . | |
| 4,639,838 | 1/1987 | Kato et al. . | |
| 4,745,526 | 5/1988 | Sestak ............ 362/804 |
| 4,785,811 | 11/1988 | Mori ............ 362/285 |
| 4,884,008 | 11/1989 | Bossler et al. . | |
| 4,924,416 | 5/1990 | Sasao ............ 362/276 |
| 5,010,460 | 4/1991 | Lin ............ 362/802 |
| 5,068,767 | 11/1991 | Koyama ............ 362/33 |

FOREIGN PATENT DOCUMENTS

| | | | |
|---|---|---|---|
| 93011 | 3/1962 | Denmark ............ | 362/804 |
| 0299196 | 1/1989 | European Pat. Off. . | |
| 2372380 | 6/1978 | France . | |
| 2536832 | 6/1984 | France . | |
| 122643 | 9/1948 | Sweden ............ | 362/804 |

*Primary Examiner*—Ira S. Lazarus
*Assistant Examiner*—Y. Quach
*Attorney, Agent, or Firm*—Sandler Greenblum & Bernstein

[57] ABSTRACT

A lamp for surgical illumination includes at least one reflector and at least one light source that are displaceable with respect to the one another by means for automatically adjusting the concentration of the light rays on an operating field. The direction of displacement of the light source or reflector is a function of the outcome of comparison, performed by a comparator, between the current algebraic value of the measurement of the luminous intensity of the light reflected by the operating field, with that of a previously performed measurement. The intensity is measured with a device which is sensitive to the light and is accommodated in a gripping handle. Touching of a sensor on the handle actuates a cycle of adjustment, in the course of which a plurality of measurements of the luminous intensity and displacements of the light source are performed jointly with the displacement of the light source, to arrive at the optimal optical concentration.

23 Claims, 4 Drawing Sheets

Fig_1

LAMP FOR SURGICAL ILLUMINATION WITH AUTOMATIC ADJUSTMENT OF THE CONCENTRATION OF LIGHT RAYS ON OPERATING FIELD

FIELD OF THE INVENTION

The present invention relates to a lamp for surgical illumination, having automatic adjustment of the concentration of light rays on an operating field.

BACKGROUND OF THE INVENTION

Surgical illumination lamps generally comprise a lamp body, in the form of an enclosure closed by a transparent panel, in which at least one light source and at least one reflector, positioned in an optical relationship with the light source are mounted, for reflecting the light rays transmitted by the source in the direction of the internal surface of the housing, toward an operating field.

Illuminating lamps generally produce a round light spot at the operating field, and the maximum luminous intensity of the illumination of the operating field is obtained with a spot of diameter whose size is predetermined in accordance each type of lamp.

Surgical illuminating lamps are equipped with mechanisms for adjusting the concentration of light rays, to obtain optimal illumination of the operating field, and these mechanisms are manually actuatable.

Adjustment of the concentration is obtained by modifying the relative position of the reflector and the light source with respect to one another. Mechanisms that enable such modification are controlled by movement of a sterilizable handle that the surgeon mounts on the illuminating lamp, in its axis.

Because this handle is located in the sterile field, it cannot be mounted and manipulated by anyone but the surgeon himself or some other person working in the sterile field.

For other types of surgically illuminating lamps, adjustment of the concentration is accomplished by control buttons that are positioned outside and lateral to the lamp housing. These control buttons are located outside the sterile field, and hence they can be operated or controlled by assistants.

In the course of a surgical operation, it is often necessary to change the position of the lamp, for example in order to illuminate the operating field from another angle. This change of position, if it involves a change in the distance between the operating field illuminated and the lamp, is accompanied by an enlargement in the area illuminated, and poorer (i.e., less intense) illumination of the operating field.

The surgeon or his assistants must then readjust the concentration of the light rays manually.

In the first instance (adjustment of the concentration by the surgeon), the surgeon is obliged to interrupt his work to perform this adjustment.

In the second instance, it is not possible to obtain a precise adjustment, because the assistants have to stay outside the sterile field.

OBJECT AND SUMMARY OF THE INVENTION

The object of the present invention is to solve the aforementioned problems by employing a lamp for surgical illumination that is provided with a mechanism for automatically adjusting the concentration of the light rays on the operating field, which mechanism is activated on the basis of the action of an element mounted on the lamp and sensitive to the touch or pressure of the surgeon's hand.

The lamp for surgical illumination according to the present invention, includes a hollow lamp body fixedly mounted to a carrier structure and provided with an opening closed off by a transparent panel in which at least one light source is provided. The light source is fixed to a support structure, and at least one reflector, in optical relation with the light source is mounted, for reflecting the light rays transmitted by the light source toward the operating field to illuminate the operating field. The light rays pass through the transparent panel on their path to the field. Manual gripping devices are provided on the lamp so as to be capable of displacing the lamp and adjusting its position with respect to the operating field.

The light source and the reflector are mounted in the lamp body so as to be capable of being displaced with respect to one another by a mechanism for adjusting the concentration of light rays on the operating field, which adjust the position of the light source and the reflector with respect to one another so that the luminous intensity of the illumination of the field will be optimized. The mechanism for automatically adjusting the concentration of the light rays on the operating field includes the following:

an apparatus sensitive to manual touch by the operator, and including at least one element intended to be touched manually by the operator. When the element is touched, an electrical signal activates the operation of adjusting the concentration of light rays;

a drive apparatus for driving the operation of adjusting the concentration of the light rays, receiving the signal, from the touch-sensitive element, for activation of an adjustment operation for adjusting the concentration of the light rays. The adjustment operation is driven by the drive apparatus only after termination of the activation signal. Termination of the activation signal occurs upon relaxation of the touch-sensitive element after the operator has released his/her touch;

a measurement device for measuring the luminous intensity of the light reflected onto the operating field, activated by the drive apparatus and including a device sensitive to light, placed facing the operating field and at a distance from it, for delivering an electrical voltage whose value is representative of the value of the luminous intensity of the light that it receives from the operating field;

at least one first memory element coupled to the measurement device, activated by the drive apparatus for driving the adjustment operation and in which, when it is activated, the algebraic value of the measurement performed by the measurement device is recorded;

at least one second memory element activated by the drive apparatus for driving the adjustment operation, and in which the algebraic value of the most recent measurement performed previously by the measurement device is recorded;

a comparison device activated by the drive apparatus for driving the adjustment operation, connected by its inputs to the first and second memory elements and by its output to the drive apparatus. When the comparison device is activated, it compares the two values recorded in the first and second memory elements and furnishes, to the drive apparatus, a signal representing the value of the algebraic difference between the value of the measurement recorded in the first memory and the value of the measurement recorded in the second memory;

a mechanism including a motor, controlled by the drive apparatus for driving the adjustment operation, mechanically coupled to the support structure of the light source and/or to the reflector in order to displace them with respect to one another and in one direction or another, the direction of displacement between these components being determined by the drive mechanism;

the drive mechanism, in the course of an adjustment operation to adjust the concentration of light rays, activates the following elements in succession:
a) the measurement device for measuring intensity,
b) the first memory element,
c) the comparison device,
d) the motor, and
e) the first and second memory elements, for recording in the second memory element the value contained in the first memory element;

and the drive apparatus, if the signal delivered by the comparison device indicates a positive or zero difference, repeats operations a, b, c and e while keeping the motor activated, in such a way as to continuously displace the light source with respect to the reflector. This displacement motion is interrupted by deactivation of the motor as soon as the signal delivered by the comparison means indicates a negative difference.

The adjustment operation may be interrupted as soon as the motor is deactivated, but in accord with an additional characteristic feature of the invention, the adjustment operation is continued, and the drive apparatus, by reactivation of the motor for a predetermined duration, controls the displacement, in an opposite direction, of the light source with respect to the reflector, and at the end of this predetermined duration deactivates the motor and interrupts the adjustment operation for adjusting the concentration.

Additionally, the length of time for which the motor is reactivated, may be proportional to the delay induced by the electronic signal processing circuits.

Further, at the onset of the adjustment operation for adjusting the concentration, the light source is displaced relative to the reflector in a predetermined direction, and the drive mechanism, by suitable control of the motor, will reverse this direction of displacement if the signal delivered by the comparison device indicates a negative difference.

Further advantages and characteristics of the invention will become apparent from the ensuing detailed description of a preferred embodiment, given by way of non-limiting example and taken in conjunction with the drawings.

DESCRIPTION OF THE PREFERRED EMBODIMENT

Figure 1:
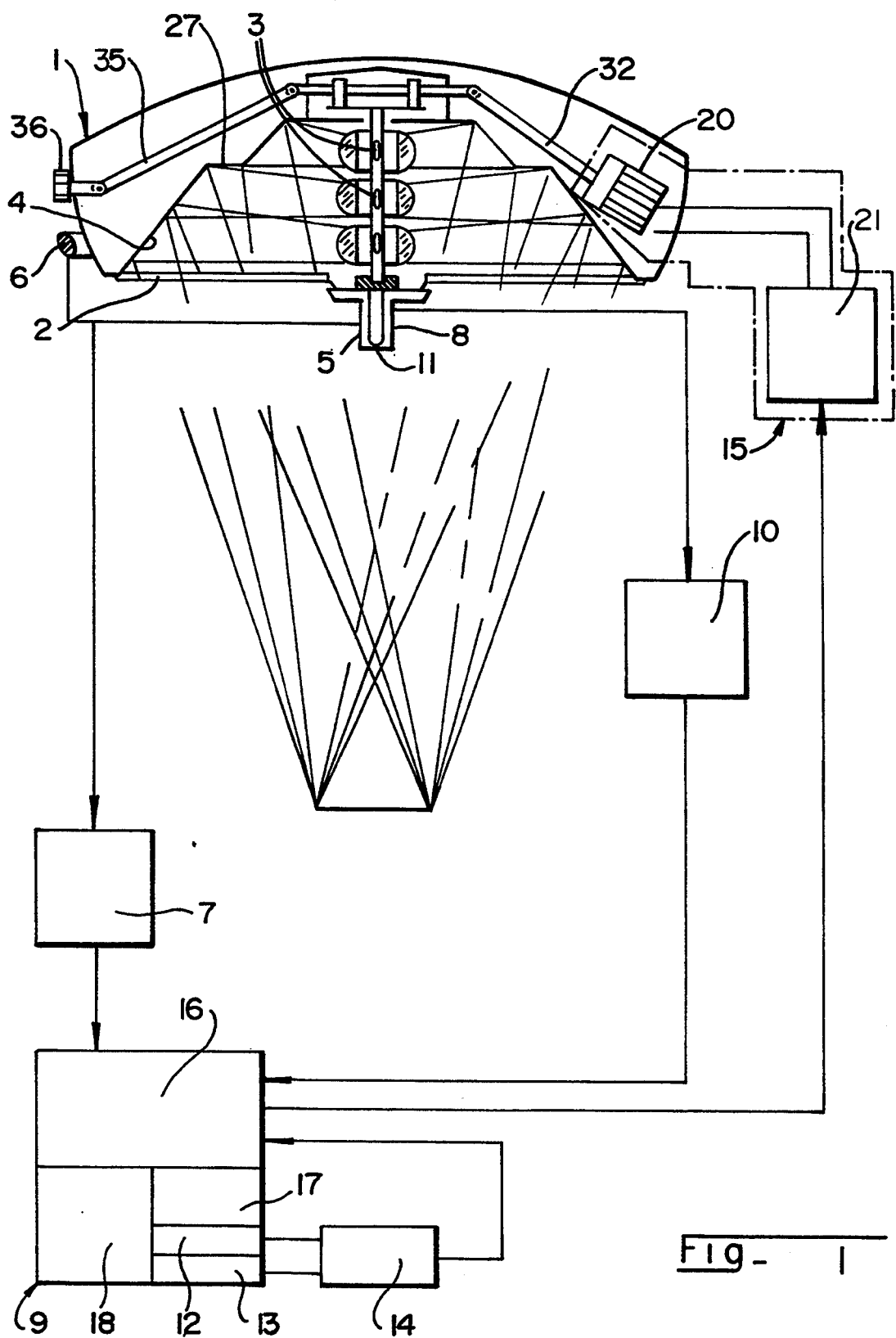
FIG. 1 is a schematic view of a lamp and adjustment mechanism according to the invention.

As shown in FIG. 1, the lamp for surgical illumination according to the present invention includes a hollow or concave lamp body 1, fixedly mounted to a carrier structure, is provided with an opening closed off by a transparent panel 2 and in which at least one light source 3 is provided. The light source is fixed to a support structure 3A, and at least one reflector 4, in optical relation with the light source, is mounted for reflecting the light rays transmitted by the light source toward the operating field, to thus illuminate the operating field. The light rays, in order to arrive at the field, pass through the transparent panel 2.

The lamp is equipped with devices 5 and 6 (such as, i.e., knobs or handles) for being gripped manually, in such a way as to enable displacement of the lamp and adjustment of its position with respect to the operating field.

These devices 5 and 6 also adjust the position of the lamp with respect to the operating field.

The light source 3 and/or the reflector 4 are mounted in the lamp body 1 with the capability of being displaced with respect to one another by a mechanism for adjusting the concentration of light rays on the operating field. This mechanism adjusts the position of the light source 3 and reflector 4 with respect to one another, in such a way that the operating field will be illuminated by light of maximum luminous intensity.

Transparent panel 2 is provided with a central cylindrical orifice, along whose periphery a central plate 1A is fixedly mounted by being secured within the body of the lamp. In addition, at its outer peripheral rim portion, the transparent panel 2 is fixed to the rim of the opening of the lamp body.

The lamp according to the present invention is also equipped with sources of electrical energy (as is conventional) that are connected to the various items of electrical equipment that it includes, in such a way as to assure a supply of electrical energy for operation of the device.

According to the invention, the means for automatically adjusting the concentration of the light rays on the operating field is described below.

An apparatus or means 7, for sensing the manual touch of the operator, includes at least one element 7A intended to be touched manually by the operator. When the element 7A of the apparatus is touched, the apparatus delivers an electrical signal for activating the adjustment operation of the concentration of the light rays.

Further, a device or means 9 for driving or controlling the adjustment operation to adjust the concentration of the light rays is provided and receives a signal for activation of the adjustment operation of the concentration of the light rays from the sensing means 7. Device 9 begins driving only after termination of the activation signal. Termination of the activation signal occurs only after release of touch and relaxation of the touch-sensitive element.

A mechanism or means 10 for measuring the luminous intensity of the light reflected onto the operating field is activated by drive means 9 and includes a device 11 that is sensitive to the light. Device 11 faces the operating field at a predetermined distance from it and delivers an electrical voltage, the value of which is representative of the value of the luminous intensity of the light that it receives from the operating field.

A first memory element 12, coupled to measurement means 10 is activated by drive means 9 for driving the adjustment operation. When memory element 12 is activated, the algebraic value of the measurement performed by measurement means 10 is recorded or stored therein.

A second memory element 13 is provided and, when activated by drive means 9 for driving the adjustment operation, records the algebraic value of the most recent measurement previously performed by measurement means 10.

A comparator device or means 14, is provided and is activated by drive means 9 for driving the operation of adjustment. Comparator device 14 is connected at its inputs, to memory elements 12 and 13, and at its output, to drive means 9. Comparator means 14, when it is activated, compares the two values recorded in the two memory elements 12, 13, and sends a signal to drive means 9. The signal represents the value of the algebraic difference between the value of the measurement recorded in the first memory and the value of the measurement recorded in the second memory.

A motor mechanism or means 15 is controlled by drive means 9 for driving the adjustment operation. Motor mechanism 15 is mechanically coupled to the support structure 3A of the light source 3 and/or to the reflector 4 in order to displace them with respect to one another and in one direction or another (i.e., in opposite directions). The direction of displacement is determined by drive means 9.

Drive means 9, in the course of the same operation of adjusting the concentration of the light rays, activates the following elements in succession: a) means 10 for measuring the intensity; b) the first memory element 12; c) comparator means 14; d) the motor 15; and e) the first and second memory elements 12 and 13 for recording in the second memory element 13 the value contained in the first memory element 12.

Driving means 9 repeats operations a, b, c and e, while keeping the motor means 15 activated, so as to continuously displace the light source 3 with respect to the reflector 4, if the signal output or delivered by the comparison means indicates a positive or zero difference. This displacement motion is interrupted by deactivation of the motor 15 as soon as the signal delivered by the comparison means indicates a negative difference.

When comparator means 14 sends a signal indicating a negative difference, this signifies and indicates that the optimal position of the light source with respect to the reflector, which would result in a maximal concentration of the light rays on the operating field, has been exceeded. If the position obtained is very close (i.e. within a predetermined error value) to the optimal position, then the adjustment operation is discontinued.

However, in a variant or further embodiment, the adjustment operation, following the output of a signal indicating a negative difference continues, by displacement of the light source in a direction opposite to the original direction of displacement with respect to the reflector, for a duration predetermined so as to approach or attain the optimal position.

In particular, this duration may take into account the delay induced by the various electronic devices of the signal processing circuits.

At the very outset of the operation of adjusting the concentration, drive means 9 controls the displacement of the light source 3 relative to the reflector 4 in a predetermined direction. If this displacement direction causes comparator means 14 to indicate a negative difference, then drive means 9, by suitable control of motor 15, will reverse the direction of displacement of the light source 3 with respect to the reflector 4.

The operation of adjusting the concentration of light then continues, subsequent to the direction reversal, as described above.

In a preferred embodiment, the element intended to be touched 7A is included in one of the manual gripping devices 5, 6.

This way, adjustment of the concentration of light rays on the operating field commences as soon as the lamp is in position.

In a preferred embodiment, the manual gripping device comprising the element intended to be touched includes a cylindrical sterilizable handle 5, fixed movably to the lamp and extending along the axis of the lamp and beneath the transparent panel.

Because handle 5 is located in the sterile field, it is not intended to be used by anyone but the surgeon or some other person working in the sterile field.

Alternatively, bail 6, fixed to the lamp body, includes the manual gripping device intended to be touched in order to trigger the operation of automatic adjustment of the concentration of the light rays.

Since bail 6 is located outside the sterile field, it can be grasped only by an assistant or some other person working outside the sterile field.

Still further, touch-sensitive element 7A may include two elements intended to be touched, which are included with each of handle 5 and bail 6, respectively.

Hence, adjusting the concentration of the light rays on the operating field can be done equally well either by the surgeon's grasping the handle, or by one of his assistants' grasping the bail.

With respect to the touch-sensitive means, the element intended to be touched is preferably formed of an electrically conductive material and is insulated from the ground of the lamp.

It should also be noted that the electrical energy supply network for the various items of equipment in the operating room creates an electrical field in which the element intended to be touched, of the touch-sensitive means is located, The touch-sensitive element 7A is electrically connected to an electronic circuit of the touch sensing means 7, and this circuit is capable of connecting or transmitting any variation in the intensity of the electrical current passing through it resulting from the touch of the element intended to be touched, of touch-sensitive means 7.

In a preferred embodiment, the electronic circuit of means 7 includes a filter, electrically connected, by its input to the touch sensitive element 7A of means 7, and by its output to a current rectifier, which comprises a frequency-to-voltage converter, for example. The filter is designed so as to allow only current at a frequency of 50 or 60 Hz to pass through it. One of the inputs of a threshold comparator is connected to the output of the frequency-to-voltage converter, and its other input is connected electrically to a source of reference voltage.

By its output, this comparator is connected to means 9 for driving the adjustment operation for adjusting the light concentration. The threshold comparator furnishes a signal only if the value of the voltage furnished by the converter is at least equal to the value of the reference voltage.

In this way, any unintentional triggering of the adjustment operation for adjusting the concentration of light is averted, i.e. touch-sensitive element 5 or 6 must be touched to actuate the adjustment.

The drive device or means 9 for driving the adjustment operation for adjusting the concentration of light rays on the operating field comprises, by way of example, a central processing unit 16, which is connected via data, instruction and address buses to input and output units and random access (RAM) and ready-only (ROM) memories 17 and 18, respectively. In particular, memories 17 and 18 contain the program for automatically adjusting the concentration of light rays.

The central processing unit 16 may include a microprocessor of any known type, that is adaptable to the present application.

The central processing unit 16 is connected, by one of its inputs, to the electronic circuit of the touch-sensitive means 7, so that at this input it will receive a signal indicating activation of the adjustment operation for adjusting the concentration of light rays. Thus, the operation does not proceed until the moment when this signal terminates.

As soon as the signal from touch-sensitive means 7 terminates, drive means 9 furnishes an activation signal to measurement means 10.

In a preferred embodiment, the device 11, that is sensitive to light, of measuring means 10 for measuring the luminous intensity of the light reflected onto the operating field, is mounted by being affixed to a plate 19, in the axis of the lamp, beneath the transparent panel 2.

This arrangement makes it possible to keep the space between the lamp and the operating field completely clear.

Advantageously, the sterilizable handle 5 is hollow and is provided with an opening facing the operating field, and when it is fixed on or attached to the lamp, it surrounds the light-sensitive device 11.

Plate 19 is fixed to the plate 1A by any means known to one skilled in the art (e.g. by threading, gluing, welding, etc.).

The sterilizable handle 5 is removably fixed to plate 1A by any means known to one skilled in the art (e.g. by threaded connection, clamping, spring clip. etc.).

A hollow is formed in the sterilizable handle for accommodating the sensitive element 11, and extends over the entire length of the handle. The handle is further provided with centering devices cooperating form-fittingly with centering devices mounted on the plate 1A.

This arrangement assures that the handle is perfectly coaxial both with respect to the lamp and with respect to the element 11 that is sensitive to the light of the measurement means 10.

Purely as an illustrative example, the light-sensitive device 11 comprises a photoelectric cell and means 10 for measuring the luminous intensity of the rays reflected by the operating field includes an analog/digital converter, such that the value of the measurement performed will be delivered in binary code to the first memory element 12.

The analog/digital converter is connected at its input to the light-sensitive device 11 and, at its output to the data bus of means 9 for driving the automatic adjustment operation for adjusting the light concentration.

In a preferred embodiment, a signal processing circuit comprising a clipper circuit followed by an averager followed by an integrator, is disposed between the light-sensitive device 11 and the analog-digital converter.

Preferably the first memory element 12 and the second memory element 13 are two memory elements of random access memories 17, each associated with the central processing unit 16.

Comparator means 14 may be of any known type.

Alternatively, the function of performing a comparison between the value recorded in the first memory element 12 and the value recorded in the second memory element 13 may be assumed by the central processing unit 16.

Such an arrangement functions to simplify the means for adjusting the concentration of the light rays.

As noted above, motor 15 is controlled by means 9 for driving the adjustment operation and is mechanically coupled to the support structure 3A of the light source 3 and/or the reflector 4 for displacing them with respect to one another.

In addition, the light source 3 and the reflector 4 are displaced with respect to one another in one of two opposite directions. The direction of displacement is determined by drive means 9 as a function of the outcome of the comparison performed by comparator means 14.

The motor mechanism means include an electric DC motor 20, for example, whose rotary output shaft is connected to the support structure 3A of the light source and/or to the reflector for mechanical transmission of motion.

The electrical motor, whose output shaft may be driven in one of two opposite direction as a function of the polarity of the electrical voltage applied to its electrical input terminals, is connected by these input terminals to an electric power circuit 21, which is activated and controlled by means 9 for driving the adjustment operation.

By way of a purely illustrative example, the power circuit is connected to a source of electrical energy by way of a switch device, which is controlled to open or close by electrical control pulses delivered by means 9 for driving the adjustment operation.

In addition, this power circuit includes an inverter device inverting the direction of polarity of the electrical supply voltage of the electric motor. For inverting the polarity, this inverter is also activated by the electric pulses delivered by means 9 for driving the adjustment operation.

Any type of surgical illumination lamp in which the position of the light source 3 with respect to the reflector 4 is adjustable may be equipped with means for adjusting the concentration of the light rays according to the present invention.

Figure 2:
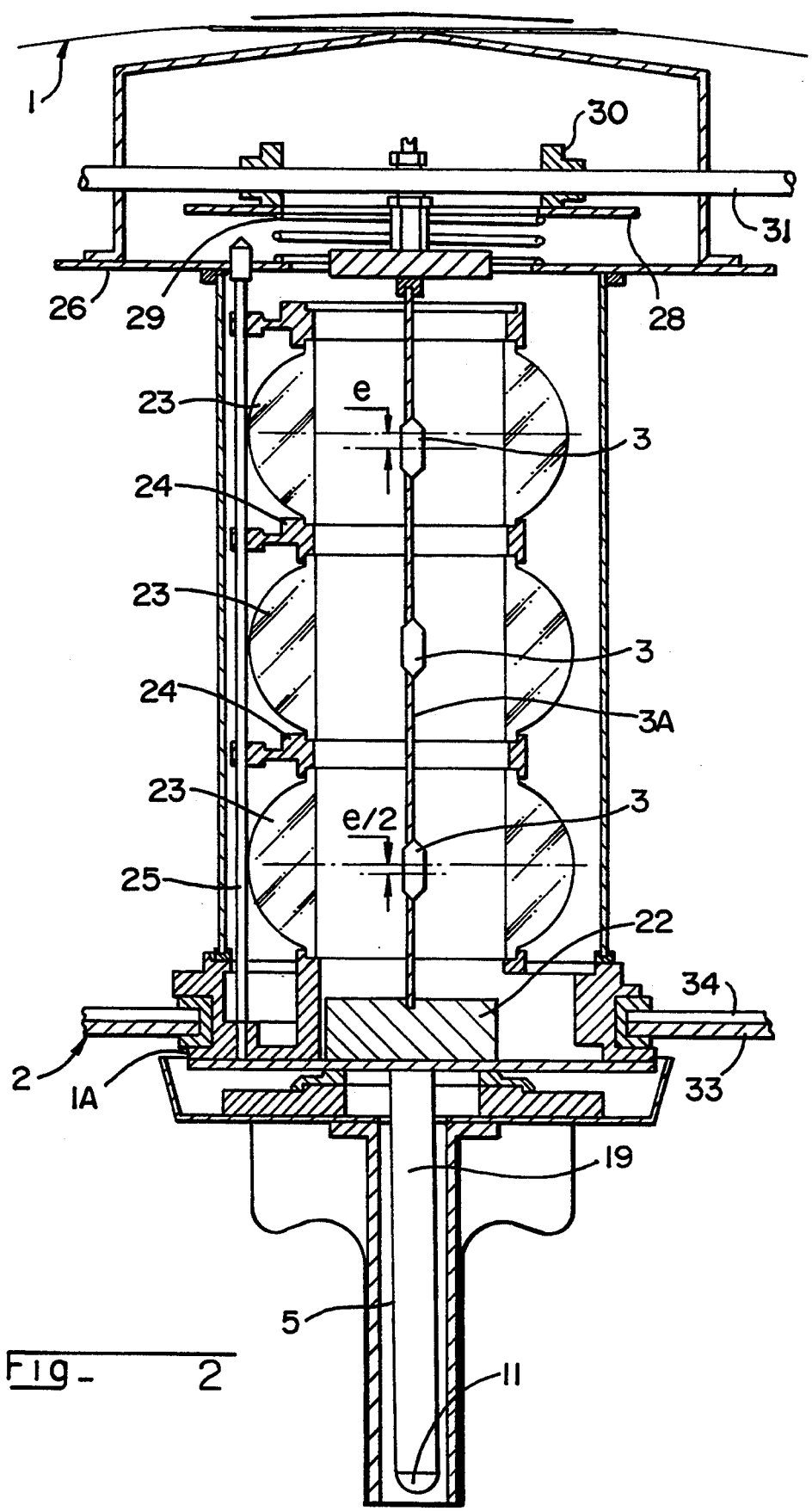
FIG. 2 is a detailed sectional view of a lamp according to the invention.
Figure 3:
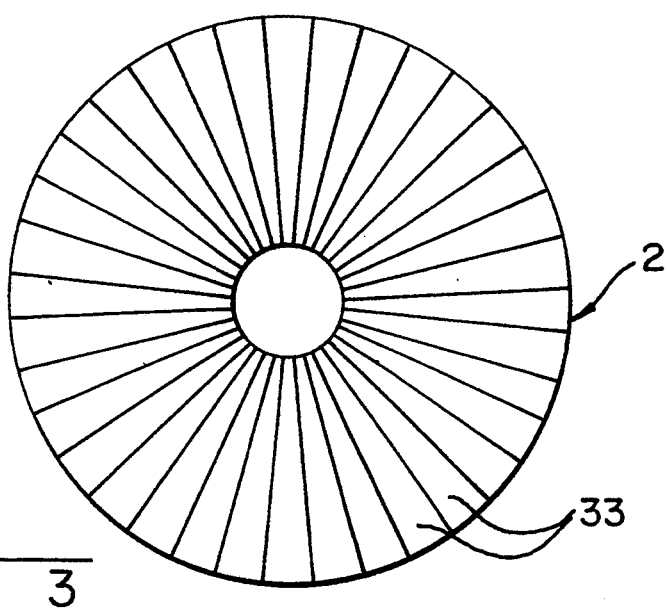
FIG. 3 is a plan view of the transparent panel of the lamp.
Figure 4:
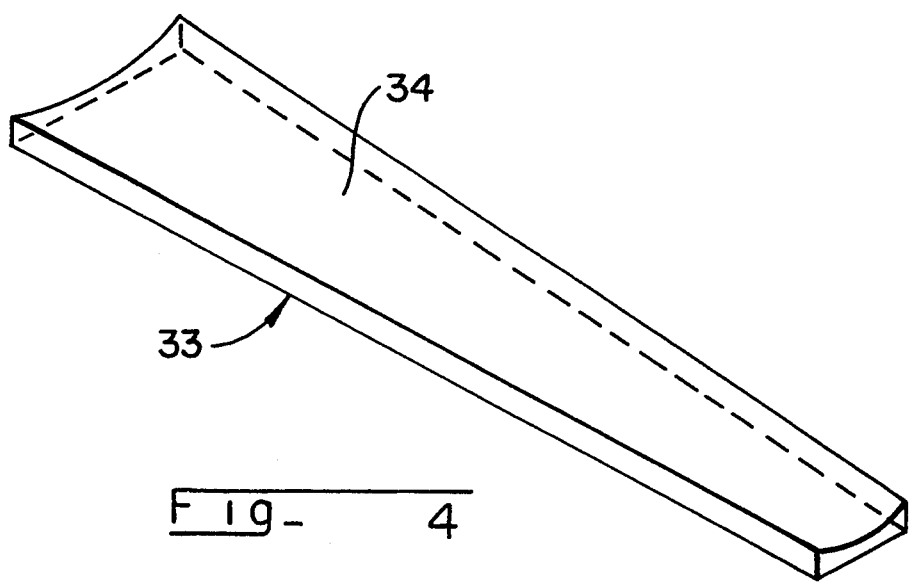
FIG. 4 is a perspective view of one element of the transparent panel of the lamp.
Figure 5:
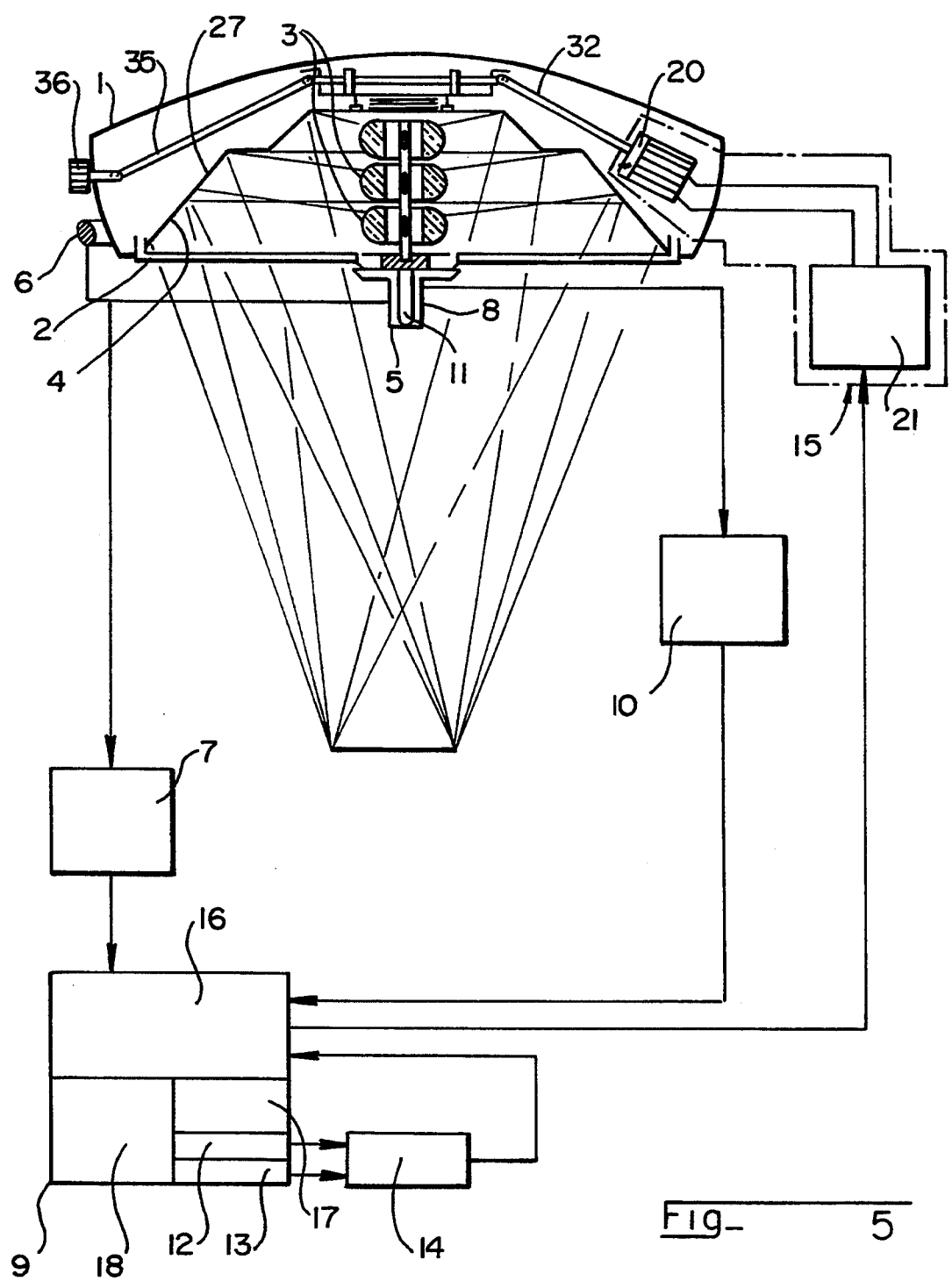
FIG. 5 is a schematic view of another embodiment of the lamp and adjustment mechanism according to the invention.

FIGS. 1 and 2 show such a lamp. The lamp shown in this drawing includes at least one displaceable light source 3 and at least one reflector 4 mounted in a fixed manner in the lamp body 1. FIG. 5 shows an embodiment where the light source 3 is fixedly attached within the lamp body 1, and the reflector 4 is connected to at least one of the motor 20 via actuating rod 32 for automatic movement and the second actuating rod 35 for movement by adjusting knob 36.

The lamp in these drawings is preferably equipped, along the axis of symmetry of the lamp body, with three light sources 3, for example, mounted spaced apart from one another along the axis of symmetry of the lamp body, on a common support structure 3A extending within the lamp body 1 along its axis of symmetry.

The support structure 3A includes at least two posts, parallel to the longitudinal axis of the lamp, which are spaced apart from one another and are kept spaced apart from one another by braces.

The light sources are fixedly mounted between the posts of the support structure.

The bottom end of the support structure includes a base 22 to which the posts are fixed. This base engages a translational guidance receptacle provided in the central plate 1A. By its upper terminal zone, the support structure cooperates with means for translational movement along the axis of symmetry of the lamp body.

Surrounding each light source 3 is an optical collar or sleeve 23 which has an inner cylindrical surface, the axis of which coincides with the axis of symmetry of the body of the housing, and a convex outer surface generated by revolution of a convex line around the outside of the light source 3.

Accordingly, the lamp is equipped with as many coaxial optical collars as light sources utilized. The collars are fixed to spacer braces 24, which are rigidly fixed to a carrier structure fixed within the housing body.

The carrier structure may include tension rods 25, affixed at the bottom ends to the central plate 1A and at the upper ends to an upper wall 26 fixed in the lamp body.

By modifying the axial position of the light source in the corresponding optical collar, the orientation of the beam of light emitted by this collar, and consequently the angle of reflection of the lights rays on the reflector 4, are modified with respect to the axis of symmetry of the collar.

In the preferred embodiment, the lamp, as shown in FIG. 1, is equipped with two coaxial reflectors 4, for example, having a frustoconical reflective surface, mounted in the lamp body one above the other and around the optical collars. The reflectors and collars are mounted coaxially with one another.

The upper reflector is intended to reflect the light rays from the upper light source and its optical collar, while the lower reflector reflects the light rays of the other two light sources and their associated optical collars.

The upper reflector is fixed by its upper rim to the upper wall 26 and by its lower rim to a ring-shaped median wall 27, to which the lower reflector is fixed by its upper rim.

The lower reflector is fixed by its lower rim to the rim of the opening of the lamp body 1.

The apex angle of the conical surface along which the reflective surface of the upper reflector extends is preferably much larger than the apex angle of the conical surface along which the reflective surface of the lower reflector extends.

Furthermore, the diameter of the lower rim of the upper reflector is smaller than the diameter of the upper rim of the lower reflector.

In addition, when one of the light sources 3 is placed in the plane of symmetry of its optical collar, the other two are offset with respect to the plane of symmetry of their respective collars. This plane of symmetry is the plane perpendicular to the axis of the lamp body.

In the embodiment shown in FIG. 1, in which three light sources, three optical collars and two reflectors are shown, it will be noted, as shown in more detail in FIG. 2, that the middle light source is placed along the plane of symmetry of its collar, while the upper light source is below the plane of symmetry of its collar and spaced from it by a value equal to e. The lower light source is below the plane of symmetry of its collar and is spaced apart from that plane by a value equal to e/2.

Because of these characteristics, the light sources 3, each in association with an optical collar and a reflector, produce beams of light which, regardless of the position of the light sources in their respective optical collars, will be superimposed on one another or will mix with one another in a single geometric plane perpendicular to the axis of the lamp.

Projected onto this single geometric plane, the beams each form a light spot having a diameter which is the same as the diameter of the light spot formed by each of the other two light sources.

Hence it will be understood that a maximum concentration of light rays corresponds to this plane of superposition.

The distance of this plane from the lamp depends on the position of the light sources in their collars.

Thus the displacement of this plane of superposition is obtained by axial displacement of the light sources 3.

Adjusting the concentration is performed by changing the position of this plane of superposition to coincide with that of the operating field.

As noted above, the support structure 3A cooperates, at its upper end, with means for translationally driving along the axis of symmetry of the lamp body. The means for translationally driving are actuated by way of the transmission of motion from the electric motor 20.

In the preferred embodiment, the translational drive means include, a pressure plate 28, fixed to the terminal zone of the structure 3A, and pushed by the action of an elastic device 29 (such as a spring) against the peripheral rim of at least one eccentric 30, which is fixed against relative rotation with respect to a shaft 31, which is mounted for rotation in two bearings and coupled by way of a cardan joint to an actuating rod 32, which is also coupled to the output shaft of the motor 20 by way of a cardan joint.

The actuating rod 32 performs the aforementioned transmission of movement from the motor to the translational drive means.

The electric motor is preferably accommodated in the lamp body and is fixed to it.

The elastic device 29 includes a spring with non-contiguous spirals. The spring is supported on the upper wall 26. This wall is pierced in its center for the passage of the upper end of the support structure 3A. The bearings (not shown) are mounted in the legs of a U-shaped stirrup 26A fixed to the upper wall 26. The actuating rod 32 is housed in the space between the reflectors and the lamp body.

To enable manual adjustment of the concentration of light rays on the operating field, a second actuating rod 35 is coupled to the shaft 31 by way of a cardan joint and is also coupled by way of a cardan joint to an adjusting knob 36 outside the lamp body.

So that the illumination of the operating field can be accomplished without extensive shadows, the transparent panel 2 includes a plurality of identical radial diopter elements 33, disposed side by side and each matching the contour of a circular ring sector, the upper face 34, of each dioptric element, being part of a conical surface having a radius of curvature that decreases from the outer peripheral rim of the panel 2 toward its center.

Preferably, the upper face of each dioptric element is concave, but it may also be convex.

Hence each dioptric element will form a light spot on a plane, the spot matching the contour of a quadrilateral.

The lamp as described will also be equipped with end of travel limit sensors associated with the output shaft of the motor, for example, in order to physically define the extreme top and bottom positions of the support structure 3A of the light sources.

A torque limiter may also be attached to the electric motor 20.

The lamp according to the invention may also be equipped with means for adjusting the luminous intensity of the light output by the light source or sources, these means being capable of, for example, controlling the supply current to these light sources.

An athermanous wall may also be disposed around the optical collars.

It will be understood that any arrangements and variants in the field of technical equivalents may be made to the illuminating lamp as described, without department from the spirit and scope of the invention as defined in the ensuing claims.

What is claimed is:

1. A lamp for surgical illumination, comprising:

a hollow lamp body fixedly mounted to a carrier structure, said hollow lamp body including an opening closed off by a transparent panel;

at least one light source fixed to a support structure and at least one reflector positioned in optical relation with said at least one light source mounted within said lamp body for reflecting light rays transmitted by said at least one light source toward a surgical operating field to illuminate the operating field so that light rays pass through said transparent panel before reaching the operating field;

at least one manual gripping device associated with said lamp body to enable manual displacement of said lamp body for adjusting the position of said lamp body with respect to the operating field;

said at least one light source and said at least one reflector being displaceably mounted within said hollow lamp body for movement with respect to one another;

means for measuring luminous intensity of the light reflected onto the operating field, said means for measuring including a device sensitive to light which is positioned facing the operating field and at a predetermined distance from the operating field, wherein, upon receiving reflected light, said means for measuring sends an electrical signal, the voltage of which is representative of the value of the luminous intensity of the light that said sensitive device receives from the operating field; and means for automatically adjusting the concentration of the light rays on the operating field, by performing an adjustment operation including adjusting the position of at least one of said at least one light source and said at least one reflector with respect to one another in such a way that the luminous intensity of the illumination of the operating field is optimized, comprising:

means for sensing the touch of an operator;

means for driving the adjustment operation of the concentration of the light rays in association with said means for sensing the touch of an operator;

a first memory element coupled to said means for measuring, activated by said means for driving the adjustment operation, said first memory element, when activated, storing the value of said electrical signal sent by said device sensitive to light of said means for measuring;

a second memory element, activated by said means for driving the adjustment operation, said second memory element, when activated, storing the value of the electrical signal corresponding to the most recent measurement previously performed by said means for measuring;

comparator means for comparing said two values recorded in said first and second memory elements, activated by said means for driving the adjustment operation, having inputs connected to said memory elements and an output connected to said means for driving the adjustment operation, said comparator means, when activated, comparing said two values recorded in said first and second memory elements, and outputting to said means for driving the adjustment operation a signal representing the value of the algebraic difference between said value of the measurement recorded in said first memory element and said value of the measurement recorded in said second memory element; and motor means, controlled by said means for driving the adjustment operation, mechanically coupled to at least one of said support structure of said at least one light source or said at least one reflector for displacing said at least one light source and said at least one reflector with respect to one another in at least one of two opposite directions along an optical axis, the direction of displacement being determined by said means for driving the adjustment operation;

said means for sensing the touch of an operator comprising at least one element adapted to be manually touched by an operator, whereby when said element is touched, said means for sensing sends an electrical activation signal for actuation to said means for driving the adjustment operation of the concentration of the light rays.

2. The lamp for surgical illumination in accordance with claim 1, wherein said means for driving, in the course of an adjustment operation for adjusting the concentration of the light rays, activates the following elements in succession:

a) said means for measuring the intensity,
b) said first memory element,
c) said comparator means,
d) said motor means,
e) said first and second memory elements to record in said second memory element, the value contained in said first memory element which was recorded in step b, and wherein said means for driving, if the signal delivered by said comparator means indicates a positive or zero difference, repeats operations a, b, c and e while keeping said motor means activated, so as to continuously displace said at least one light source with respect to said at least one reflector in a predetermined direction, said means for driving interrupting the displacement motion of said at least one light source by deactivation of said motor means when the signal delivered by said comparator means indicates a negative difference.

3. The lamp for surgical illumination in accordance with claim 1, said lamp body defining an axis of symmetry; said at least one light source comprising a plurality of light sources mounted spaced apart from one another, along said axis of symmetry of said lamp body, on a common support structure;

said common support structure having a lower and including a base, an optical collar disposed around each said light source, each said optical collar having a cylindrical inner surface with an axis coinciding with the axis of symmetry of said lamp body and having a convex outer surface generated by revolution of a convex line around said light source; and said common support structure with said base, engaging a translational guide receptacle formed in a central plate, and cooperating, at its upper end, with means for translational movement along the axis of symmetry of the lamp body.

4. The lamp for surgical illumination in accordance with claim 3, said at least one reflector comprising upper and lower coaxial reflectors with frustoconical reflective surfaces mounted in the lamp body around said optical collars.

5. The lamp for surgical illumination in accordance with claim 4, said reflector upper having an apex angle of the conical surface along which the reflective surface of said upper reflector extends larger than the apex angle of the conical surface along which the reflective surface of said lower reflector extends.

6. The lamp for surgical illumination in accordance with claim 5, wherein said lamp body has an axis, and beams of light produced by said light sources in association with said optical collars and said reflectors are superimposed in a single geometric plane perpendicular to the optical axis of the lamp body.

7. The lamp for surgical illumination in accordance with claim 3, wherein each said optical collar defines a plane of symmetry, and when one of said light sources is positioned in said plane of symmetry of its optical collar, the other of said light sources are offset with respect to the plane of symmetry of their optical collars.

8. The lamp for surgical illumination in accordance with claim 1, wherein said means for sensing the manual touch of an operator is located within said at least one manual gripping device.

9. The lamp for surgical illumination in accordance with claim 8, said at least one manual gripping device comprises said means for sensing the manual touch of an operator and comprises a bail fixed to said hollow lamp body.

10. The lamp for surgical illumination in accordance with claim 1, wherein said lamp body has an optical axis, and said at least one manual gripping device comprises said at least one element adapted to be manually touched, and comprises a cylindrical sterilizable handle, said cylindrical sterilizable handle being removably fixed to the lamp body and extending along the optical axis of the lamp body and beneath said transparent panel.

11. The lamp for surgical illumination in accordance with claim 10, wherein said sterilizable handle is hollow and is provided with an opening facing the operating field, and surrounds said light sensitive device upon being fixed to the lamp body.

12. The lamp for surgical illumination in accordance with claim 1, wherein said lamp body has an optical axis, and said light sensitive device is fixedly mounted to a plate and positioned along the optical axis of the lamp body, beneath said transparent panel.

13. The lamp for surgical illumination in accordance with claim 12 further comprises a hollow sterilizable handle is hollow and is provided with an opening facing the operating field, and surrounding said light sensitive device when said handle is secured.

14. The lamp for surgical illumination in accordance with claim 13, said lamp body defining an axis of symmetry; said at least one light source comprising a plurality of light sources mounted spaced apart from one another, along said axis of symmetry of said lamp body, on a common support structure;

said common support structure having a lower end including a base, an optical collar disposed around each said light source, each said optical collar having a cylindrical inner surface with an axis coinciding with the axis of symmetry of said lamp body and having a convex outer surface generated by revolution of a convex line around said light source; and said common support structure with said base, engaging a translational guide receptacle formed in a central plate, and cooperating, at its upper end, with means for translational movement along the axis of symmetry of the lamp body.

15. The lamp for surgical illumination in accordance with claim 1, said at least one element intended to be manually touched comprising an electrically conductive material insulated from the ground of the lamp.

16. The lamp for surgical illumination in accordance with claim 15, said manual touch-sensing means comprising an electronic circuit for detecting variations in intensity of an electrical current resulting from touching of said at least one element intended to be manually touched.

17. The lamp for surgical illumination in accordance with claim 1, said at least one reflector being fixed and said at least one light source being displaceable.

18. The lamp for surgical illumination in accordance with claim 1, said transparent panel comprising an outer peripheral rim, a center portion and a plurality of substantially identical radial dioptric elements including an upper face disposed side by side, each said radial dioptric element matching the contour of a circular ring section, said upper face of each said dioptric element forming a portion of a conical surface having a radius of curvature that decreases from said outer peripheral rim of said panel toward said center portion of said panel.

19. The lamp for surgical illumination in accordance with claim 18, wherein said upper face of each said radial dioptric element is concave.

20. The lamp for surgical illumination in accordance with claim 18, wherein said upper face of each said radical dioptric element is convex.

21. The lamp for surgical illumination in accordance with claim 1, wherein following deactivation of said motor means, when said comparator means outputs a signal having a negative value, said drive means reactivates said motor means for a predetermined duration to control the displacement of said at least one light source and said at least one reflector with respect to one another, in a direction opposite said direction and, at the end of the predetermined duration, deactivates said motor means and interrupts the adjustment operation.

22. The lamp for surgical illumination in accordance with claim 1, said drive means controlling displacement of said at least one light source with respect to said at least one reflector in a predetermined direction, and, further controlling said motor means to reverse the displacement direction if said signal outputted by said comparator means indicates a negative difference.

23. The lamp for surgical illumination in accordance with claim 1, wherein said means for driving drives the adjustment operation only after said electrical activation signal terminates as a result of relaxation of said touch-sensitive element in response to the operator's release of touch.

\* \* \* \* \*

UNITED STATES PATENT AND TRADEMARK OFFICE
CERTIFICATE OF CORRECTION

PATENT NO. : 5,383,105
DATED : January 17, 1995
INVENTOR(S) : Gerard AGUT

It is certified that error appears in the above-indentified patent and that said Letters Patent is hereby corrected as shown below:

At column 13, line 3 (claim 3, line 7), change "and" to ---end---.

At column 13, line 21 (claim 5, line 2), change "reflector upper" to ---upper reflector---.

At column 13, line 27 (claim 6, line 2), change "axis" to ---optical axis---.

At column 13, line 66 (claim 13, line 3), delete "is hollow and is".

At column 14, line 45 (claim 20, line 3), change "radical" to ---radial---.

Signed and Sealed this

Twelfth Day of March, 1996

Attest:

BRUCE LEHMAN

Attesting Officer        Commissioner of Patents and Trademarks